United States Patent [19]

Colton

[11] Patent Number: 4,983,408
[45] Date of Patent: Jan. 8, 1991

[54] METHOD FOR PRODUCING COFFEE EXTRACTS

[76] Inventor: Ralph L. Colton, 101 Tanglewood Dr., Lansdale, Pa. 19446

[21] Appl. No.: 280,945

[22] Filed: Dec. 7, 1988

[51] Int. Cl.$^5$ .............................................. A23F 5/10
[52] U.S. Cl. ...................................... 426/45; 426/425; 426/432; 426/433; 426/434; 426/447; 426/594
[58] Field of Search ................. 426/45, 425, 432, 433, 426/434, 594, 447

[56] References Cited

U.S. PATENT DOCUMENTS

| | | | |
|---|---|---|---|
| 2,282,138 | 5/1942 | Kellogg | 426/45 |
| 2,324,526 | 6/1943 | Morgenthaler | 426/432 |
| 3,088,825 | 5/1963 | Topalian et al. | 426/447 |
| 3,106,470 | 10/1963 | Spotholz | 426/447 |
| 3,120,439 | 2/1964 | Reale | 426/432 |
| 4,540,591 | 9/1985 | Dar et al. | 426/447 |
| 4,544,567 | 10/1985 | Gottesman | 426/594 |

OTHER PUBLICATIONS

Stivetz et al., "Coffee Technology", 1979, pp. 350, 369.

*Primary Examiner*—Donald E. Czaja
*Assistant Examiner*—Evan Federman
*Attorney, Agent, or Firm*—Joseph W. Molasky & Assocs.

[57] ABSTRACT

A method for producing a coffee extract which comprises: (1) contacting an aqueous mixture of ground roast coffee with steam under pressure at elevated temperatures followed by rapid decompression at atmospheric levels; and (2) treatment of the resulting mixture with a hydrolytic enzyme or with a mixture of hydrolytic enzymes. The coffee extract thus obtained is a concentrated liquid which can be made into a beverage by the addition of water or it may be dried to a soluble solid and reconstituted with water to provide instant coffee.

17 Claims, No Drawings

METHOD FOR PRODUCING COFFEE EXTRACTS

This invention relates to a novel method for obtaining coffee extracts in high yield by subjecting ground roasted coffee or partially extracted coffee to high steam pressure and elevated temperatures followed by rapid decompression to atmospheric levels. The resulting substrate is then subjected to enzymatic hydrolysis to afford an extract which can be reconstituted into a beverage by the addition of water.

BACKGROUND

Coffee extract, to the industry, is considered to be an aqueous solution of soluble solids extracted from the coffee bean. It is an intermediate stage product in the manufacture of freeze-dried and spray-dried (regular instant) coffees. It is also used directly in flavorings and in certain vending operations.

Until and even after World War II, coffee extract was batch-brewed from roasted and ground coffee and then dried. The flavor was poor, in part because of technical problems in dehydration. The dried product was hygroscopic and caked readily while reconstituting poorly. However, it was welcomed in the Army C Ration which gave a boost to post-war product acceptance.

Later, it was found that the addition of malto-dextrin (corn syrup) improved the flavor by aiding the dehydration process, reduced hygroscopiscity (caking), greatly aided reconstitution and made measurement more convenient.

Intense post-war competition as companies crowded into this rapidly growing market called for selling a "pure instant coffee". The expended coffee grounds became the obvious source of solubles to replace malto-dextrin. There were three potential approaches:

1. The first was enzymatic hydrolyzation. It had many potential advantages. However, this approach was abandoned because the yield of solubles obtainable was too low to be commercially feasible.

2. Acid hydrolysis; this was highly effective but required salt removal when the pH was restored to acceptable levels for the beverage. It was represented by U.S. Pat. Nos. 2,573,405 and 2,687,399 but was rejected by the industry.

3. High temperature, high steam-pressure hydrolysis; was first used commercially in 1950 and soon became the system of choice worldwide in the manufacture of instant coffee. Morganthaler was issued U.S. Pat. No. 2,573,405 in 1943 covering this process.

This process utilizes high temperature (up to 175° C.), high steam-pressure hydrolysis. The residence time is long, up to 2-3 hours.

The process and its operating problems and limitations are described in detail in "Coffee Processing", Volume 2, Sivetz & Foote, 1963 and in the updated version, "Coffee Technology", Sivetz & Desrosier, 1979, both by AVI Publishing.

Using the Morganthaler process the industry's standard yield of soluble solids (dry weight basis) based on the weight of the green coffee used grew to 40%. This varies, of course, depending on the raw material source, degree of roast and other operating conditions.

It is recognized in the industry that an increase of only 5° C. above the patent's 175° C. can degrade the substrate in only "15-30 minutes together with the extract thereby produced and results in an unacceptable product". Increased residence time beyond the 2-3 hours standard in the industry results in an "over extracted", undrinkable beverage. (References: "Coffee Processing", Volume 2 and "Coffee Technology" referred to above).

Besides the limitation to higher yields described above, the liquid coffee extract produced by this system has deficiencies of gel formation (undesirable when the concentrate is used for liquid coffee vending) and viscosity which limits evaporative concentration which would permit optimal utilization of the dehydrators. Enzymes are used in reducing these problems. (See U.S. Pat. No. 2,801,920, 1957).

In 1942 there were issued to John L. Kellogg U.S. Pat. Nos. 2,282,138 and 2,282,139. The concepts patented, including the use of an enzyme (diastase) and "relatively high steam pressure" as a pre-treatment of the ground roasted coffee to increase the yield of solubles were major advances in soluble coffee technology.

Kellogg called for using a converting enzyme diastase ("preferably Taka-diastase", Takemine U.S. Pat. No. 1,391,219, 1921) at temperatures of 125°-135° F. after pre-treating the coffee at 15 psi for one hour "to soften and loosen the fibres". He refers to obtaining and preserving more of the "delicate aroma" of coffee and to obtaining a "greatly enhanced yield of extractives". Unfortunately, Kellogg gave no figures to substantiate his claims. Others, trying this system, found the yield too low to be commercially practical, particularly in comparison to the yield possible using the Morganthaler process.

Kellogg was greatly interested in aroma preservation and protection from bacterial degradation which he believed his system, using taka-diastase, would provide. Although his enzymatic hydrolysis system appeared to have merit, his choice of diastase as the converting enzyme is questionable. Diastase solublizes starch, primarily to dextrose. In 1942 little was known about the chemical composition of roasted coffee. "All About Coffee", William H. Ukers, Second Edition, 1935 published by Tea & Coffee Trade Journal (the most advanced technical book at that time) acknowledges this fact.

It was not until 1985 that a substantial analysis of coffee chemistry was available. "Coffee: Botany, Biochemistry and Production of Beans and Beverage", edited by M. N. Clifford and K. C. Willson, published by Croom Held, London, reported the work of many researchers. From this it is possible to obtain an approximate chemical analysis of roasted coffee. Surprisingly, the starch content (which is the constituent which diastase solubilizes) is less than ½% according to the average of the findings reported.

The above work also indicated that cellulose makes up about 50% of the weight of roasted coffee and would, therefore, be the most important constituent to solubilize. However, "Coffee Technology", Sivetz & Descrosier, 1979, states on page 369 under the heading "Useless Techniques", "the use of enzymes to solubilize cellulose portions of green or roast coffee is impractical".

THE INVENTION

It has been found surprisingly that the difficulties associated with the use of high heat and high pressure in coffee extraction processes can be overcome by introducing the heat and pressure in a brief pre-treatment step prior to enzymatic hydrolysis.

The essence of this invention lies in the discovery that ground coffee which is subjected to a steam pre-treatment step or steam explosion affords soluble coffee solids in high yield and devoid of the bitterness associated with many known methods.

By "steam explosion" is meant placing ground coffee in a pressure vessel and contacting the contents with steam at elevated temperatures and higher than ambient pressures. The ingredients must be contacted for a period of from about 1-10 minutes and, preferably, 1-5 minutes. Temperatures in excess of 200° C. are required but temperatures in the range of from about 220°-250° C. are most desirable. This steam pre-treatment step is conducted at pressures of from about 225-450 psi and most preferably 370-450 psi for a period of up to 10 minutes followed by rapid decompression to atmospheric levels, that is, by exposing the contents of the vessel to the atmosphere so that the pressure within the vessel is instantaneously released without cooling.

Applicant does not profess to understand fully the transformation which takes place when coffee is subjected to steam explosion but it is believed that cellular rupture and pore-size enlargement occur as a result of which the surface area of the coffee substrate is increased and the ability of the hydrolyzing enzyme to effect solubilization is enhanced.

In practice, the cellular rupture attributed to the roasting of coffee beans translates into a brewing extraction of about 15-25%. By contrast, the steam explosion or steam pre-treatment of this invention is believed to cause additional cellular rupture and cellular expansion as a result of which the coffee solids present to the added enzymes a vastly increased surface area for solubilization. This steam pre-treatment procedure may be applied to green coffee, roasted coffee or partially extracted ground coffee including vegetable material such as acorns, barley and the like.

Once the steam explosion procedure has been concluded the steam-treated solids are cooled to about 30°-60° C. and brought into contact with the hydrolyzing enzyme or mixture of enzymes. The enzymes solubilize the otherwise insoluble components of the coffee solids by binding to specific receptor points. Enzymes which may be employed include, for example, the amylases, hemicellulase, cellulase, protease, cellobiase, pectinase and the lipases. These enzymes can be employed individually or in combination in relatively minor concentrations of 0.1-1.0% of enzyme concentrate relative to the substrate constituent.

Cellulose comprises about 50% of most ground roast coffee and cellulase produced from a mutant of the fungus *Trichoderma viride* (*T. reesei*) is most effective in cleaving the insoluble components into smaller molecules which are water soluble as illustrated by the reduction of glucocellulose to glucose and cellobiose.

A typical operation according to this invention consists of treating ground roast coffee with hot water in conventional extraction batteries, concentrating the extract by evaporation and retaining this first-extract for later blending.

The partially extracted coffee grounds is then extracted further by placing same in a pressure vessel and treating the contents with steam introduced at pressures of about 370-450 psi for 4 minutes. The resulting slurry is decompressed instantaneously to atmospheric pressure and the contents of the vessel are cooled to about 25°-65° C.

The cooled coffee slurry is then contacted with a hydrolytic enzyme such as cellulase to effect hydrolysis and the aqueous mixture is agitated for 3-6 hours to achieve optimum solubilization.

Once solubilization has occurred the resulting extract is separated from insoluble residues by centrifugation and the extract is concentrated by evaporation and blended with the first extract to afford a concentrated liquid extract which contains the flavors and aromas of freshly brewed coffee.

Particle size reduction enhances enzymatic contact. Increasingly smaller particle sizes, even micro-pulverization to less than 100 microns, gave increasingly greater yields as substrate pre-treatment for enzymatic hydrolysis but insufficient to be commercially practical. More extreme substrate pre-treatment was necessary to provide a larger area for enzymatic contact and studies were conducted using ground roasted coffee which was subjected to steam explosion and enzymatic hydrolysis (Example 2). The enzymes which effect the solubilization of coffee constituents are all compatible and their yields are additive.

The process of this invention can be operated continuously or batchwise. If desired, the liquid may be freeze-dried or spray-dried to afford a soluble solid which can be reconstituted by the addition of water to form beverage coffee.

This invention will now be described by referring to precise embodiments. Example 1 illustrates the enzymatic hydrolysis of expended coffee grounds absent steam pre-treatment. Example 2, on the other hand, describes the present invention and illustrates in detail the enzymatic hydrolysis of ground roasted coffee which has been first subjected to 'steam-explosion'.

EXAMPLE 1

Expended coffee grounds from brewed micro-pulverized coffee were divided into five portions each weighing 100 grams and these were identified as Samples A, B, C, D and E. To Sample A was added 75 ml of water and this mixture was designated as the Control.

Samples B, C, D and E were also mixed with water (75 ml) and the following enzymes were added:

| Sample B: | Protease | 20 mg |
|---|---|---|
| Sample C: | Cellulase | 130 mg |
| Sample D: | Hemicellulase | 10 mg |
| Sample E: | Protease | 20 mg; Cellulase 130 mg; and |
| | Hemicellulase | 10 mg. |

Samples A, B, C, D and E were placed in beakers equipped with magnetic stirrers and the mixtures were agitated and heated at a water-bath temperature of 45°-50° C. for twenty-four hours.

Following the heating period, water (100 ml) was added to each sample, the bath temperature was raised to 90° C. for 20 minutes to inactivate the enzymes, and stirring was discontinued. Sedimentation occurred and the effluents from each sample were decanted, centrifuged and dried. The sediments from each sample were also dried and the yields of dried sediment and dried effluent residue were calculated:

Sample A (Control)

| Dried Sediment: | 20.14 g |
|---|---|
| Dried Effluent Residue: | 0.82 g |

Based on this study the total yield of soluble coffee solids is 4.1% calculated as follows: 0.82 g ÷ 20.96 g × 100 = 4.1%.

Sample B (Protease)

| | |
|---|---|
| Dried Sediment: | 19.09 g |
| Dried Effluent Residue: | 1.78 g |
| Total Weight of Solids | 20.87 g |

Based on this study the total yield of soluble coffee solids is 8.5% calculated as follows: 1.78 g ÷ 20.87 g × 100 = 8.5%.

Sample C (Cellulase)

| | |
|---|---|
| Dried Sediment: | 19.57 g |
| Dried Effluent Residue: | 1.44 g |
| Total Weight of Solids | 21.01 g |

Based on this study the total yield of soluble coffee solids is 6.8% calculated as follows: 1.44 g ÷ 21.01 g × 100 = 6.8%.

Sample D (Hemicellulase)

| | |
|---|---|
| Dried Sediment: | 17.85 g |
| Dried Effluent Residue: | 3.08 g |
| Total Weight of Solids | 20.93 g |

Based on this study the total yield of soluble coffee solids is 14.7% calculated as follows: 3.08 g ÷ 20.93 g × 100 = 14.7%.

Sample E (Protease, Cellulase, Hemicellulase)

| | |
|---|---|
| Dried Sediment: | 16.34 g |
| Dried Effluent Residue | 4.72 g |
| Total Weight of Solids | 21.06 g |

Based on this study the total yield of soluble coffee solids is 22.4% calculated as follows: 4.72 g ÷ 21.06 g × 100 = 22.4%.

The combined yield of product from Samples B, C and D (17.7%) was determined by subtracting the Control Yield (4.1%) from the percent yield of Samples B, C and D and totalling the results.

On the basis of this study it was determined that the yield of product with these enzymes is additive.

The foregoing process represents the state of the art and it is to be compared with the present invention which provides for steam pre-treatment of the coffee substrate. The results of this study are shown in Example 2.

EXAMPLE 2

Step A; Steam Treatment

Ground roasted coffee was wetted and placed in a pressure vessel. Steam was introduced sufficient to raise the temperature to 225° C. and produce a pressure of 370 psi. After 4 minutes the pressure was instantaneously reduced to atmospheric conditions and the treated grounds were cooled to room temperature.

Step B; Enzymatic Hydrolysis

The grounds obtained according to Step A were divided into two 100 g portions. Water (75 ml) was added to one portion and the mixture was identified as Sample R (Control). Water (75 ml), hemicellulase (15 mg) and cellulase (135 mg) were added to the second portion and this mixture was designated as Sample S.

Samples R and S were maintained at a water-bath temperature of 45°-50° C. for three hours with stirring following which water (75 ml) was added to each sample and their respective temperatures raised to 90° C. After twenty minutes stirring was discontinued, sedimentation was allowed to occur, the effluents were poured from each sample and the residue centrifuged. The effluents and sediment were then dried to afford the following yields of soluble coffee solids:

Sample R (Control)

| | |
|---|---|
| Dried Sediment: | 15.28 g |
| Dried Effluent Residue: | 12.03 g |
| Total Weight of Solids: | 27.31 g |

The total weight of effluent (aqueous extract of coffee) was 170.77 g which contained (as shown above) 12.03 g of soluble coffee solids.

Based on this study the total yield of soluble coffee solids is 44.0% calculated as follows: 12.03 g ÷ 27.31 g × 100 = 44.0%.

Sample S (Hemicellulase and Cellulase)

| | |
|---|---|
| Dried Sediment: | 12.53 g |
| Dried Effluent Residue: | 14.09 g |
| Total Weight of Solids: | 26.62 g |

The total weight of effluent (aqueous coffee extract) was 174.41 g which contained, as shown above, 14.09 g of soluble coffee solids.

Based on this study the total yield of soluble coffee solids is 52.9% calculated as follows: 14.09 g ÷ 26.62 × 100 = 52.9%.

The standard yield in soluble coffee manufacturing is 40% from green beans which is adjusted to 48.2% from roasted coffee after allowing for a 17% roasting loss. For example, a 60 kg bag of green coffee will afford 24 kg of dry coffee solubles. After medium roasting with a 17% loss in weight, a 60 kg bag of green coffee affords 49.8 kg of roasted coffee. The 24 kg of dried coffee solubles divided by 49.8 indicates a yield of 48.2% of coffee solubles.

This study demonstrates the improved yield of soluble coffee (52.9% versus 48.2% as shown above) obtained by subjecting ground roasted coffee to steam treatment and rapid decompression prior to enzymatic hydrolysis.

The result of the test recorded as Example 2 was highly satisfactory, giving yields substantially above that which is standard in the industry.

A test was also made using various levels of steam pre-treatment using 15 psi pressure (recommended by Kellogg in U.S. Pat. No. 2,282,138), 225 psi (200° C.) and 370 psi (225° C.) and the results of this study are presented in Example 3.

EXAMPLE 3

Five equal portions of roasted regular ground coffee were placed in beakers designated as Samples A, B, C, D and E and mixed with 75 ml of water. These aqueous mixtures were treated as follows:

Samples A and B

Sample A was pre-treated with steam at 225° C. and 370 psi in an autoclave. After 4 minutes the autoclave was opened to the atmosphere. The slurry was diluted with water to approximately 20% solids by weight, brought to ambient temperature and treated with cellulase (Novo Industri "Celluclast", 1.5 L) at 1% of the estimated cellulose content.

Sample A was maintained in a water bath at 45°–50° C. for 3 hours and decanted according to the procedure described in Example 1, supra. The decanted effluent was vacuum-dried and the sediment was oven-dried. The yield of coffee extract was measured and calculated at 44.1%.

Sample B was treated in a manner identical to that of Sample A except that the temperature of the autoclave was maintained at 200° C. and the pressure maintained at 225.6 psi. The yield of coffee extract was measured and calculated at 24.4%.

Sample C

Sample C was treated in a manner identical to that of Sample A except that the aqueous coffee mixture was brought to approximately 20% solids by weight before being subjected to pressure-cooking for 1 hour at approximately 120° C. and 15 psi.

The cooled coffee mixture was then treated with cellulase at 1% of the estimated cellulose content.

The sample was maintained at a water bath temperature of 45°–50° C. for 3 hours and otherwise processed according to the procedure described for Sample A, supra. The yield of dried coffee extract was measured and calculated at 21.7%.

Sample D

To the sample identified as Sample D, a slurry containing approximately 20% solids by weight, there was added 130 mg of cellulase (Nova Industri "Celluclast", 1.5 L).

This sample was maintained at a water bath temperature of 45°–50° C. with stirring. After 3 hours water (75 ml) was added and the temperature was raised to 90° C., again with stirring. After 20 minutes the stirring was discontinued, sedimentation was allowed to occur and the effluent was poured from the sample and the residue centrifuged. The effluent was dried to afford a 20.7% yield of coffee extract.

Sample E

The sample identified as E was treated according to the procedure set forth for Sample D except that the enzymatic hydrolyzation step was omitted. The yield of coffee extract obtained according to this procedure was 18.9%.

A summary of the reaction conditions employed in this study and the yields of coffee extracts obtained are set forth in the following Table. The entries under "Steam Treatment" describe the procedure to which the ground coffee samples were subjected, if any, prior to enzymatic hydrolysis.

TABLE I

| SAMPLE | STEAM TREATMENT | TEMPERATURE | PRESSURE | TIME | ENZYME | YIELD |
|---|---|---|---|---|---|---|
| A | Steam-Explosion | 225° C. | 370 psi | 4 mins. | Cellulase | 44.1% |
| B | Steam-Explosion | 200° C. | 225.6 psi | 4 mins. | Cellulase | 24.4% |
| C | Pressure-Cooked | 121° C. | 15 psi | 60 mins. | Cellulase | 21.7% |
| D (Control) | None | — | — | — | Cellulase | 20.7% |
| E (Control) | None | — | — | — | None | 18.9% |

The results in Table I demonstrate that pre-treatment of ground coffee samples with steam at temperatures of at least 225° C. results in a significantly greater increase in yield of coffee extract (44.1%) when compared to the yields obtained at 200° C. (24.4%).

Moreover, the combination of steam pre-treatment with enzymatic hydrolysis results in even greater yield enhancement when the results of Sample A are compared with Sample E (44.1% v 18.9%).

On the basis of this study it has been concluded that the steam pre-treatment of coffee mixtures at temperatures of 225° C. and greater over periods ranging from about 1–5 minutes significantly enhances the yield of soluble coffee extracts.

Cellulase was used in this test instead of diastase since there is about 100 times more cellulose than starch in roasted coffee and yield differences would, therefore, be more readily observable when comparing the results of the various pre-treatment steam pressures.

It is clear from this test (Table I) that an increase in the severity of the pre-treatment of a magnitude 12–15 times that of the pressure advocated by Kellogg is necessary for satisfactory enzymatic hydrolysis.

In addition to a high yield of soluble solids, enzymatic hydrolysis provides a number of other advantages over the Morganthaler process. It was discovered that, since each class of enzyme is specific as to the coffee constituent which it will solubilize, that a final product with enhanced flavor characteristics can be obtained. Bitterness is often a problem in soluble coffee manufacturing because protein, when solublized, is converted into amino acids and peptides some of which are bitter. The known methods have no selectivity and hydrolysis depends on time and temperature only. In enzymatic hydrolysis, the protein will remain in the final residue if the converting enzyme, protease is not used. Thereby, the bitterness factor contributed by protein solubilization can be largely avoided.

Another substantial advantage results from leaving the protein in the final residue. Because of steam explosion, the residue is digestible to cattle. The residue from the use of the Morganthaler process is not. Roasted coffee contains 10–12% protein. After extraction using enzymatic hydrolysis without using protease, the final residue should contain about 20% protein which would make a highly nutritious as well as digestible cattle feed.

While it appears obvious that this invention is a major improvement over the Kellogg Patents, its usefulness in the market-place is dependent on the following commercial advantages:

1. The yield of soluble solids is substantially greater than that obtainable by the Morganthaler process.

2. The product quality (flavor) can be better than that possible by the Morganthaler process.

3. Energy and other costs are lower than those associated with the Morganthaler process.

4. The operating problems using enzymatic hydrolysis are substantially less than those using high temperature, high steam-pressure hydrolysis.

5. The final residue is a digestible and nutritious cattle feed which is useful as a high value by-product.

This invention has been described by reference to precise embodiments but it will be appreciated by those skilled in the art that this invention is subject to various modifications and to the extent that those modifications would be obvious to one of ordinary skill they are considered as being within the scope of the appended claims.

What is claimed is:

1. A method for producing an improved yield of coffee extract which comprises:
   (1) pre-treating an aqueous mixture of ground roast coffee with steam in a closed vessel under pressure at a temperature in excess of 200° C.;
   (2) maintaining said temperature and pressure for a period of from about 1-10 minutes;
   (3) instantaneously exposing the contents of said vessel to the atmosphere without cooling so as to bring said contents to atmospheric levels; and
   (4) treating the slurry thus obtained with a member selected from the group consisting of a hydrolytic enzyme and a mixture of hydrolytic enzymes.

2. The method according to claim 1 wherein the desired product is obtained as a concentrated effluent.

3. The method according to claim 2 wherein the concentrated effluent is dried to a soluble solid.

4. The method according to claim 1 wherein the pre-treatment procedure of Step (1) is conducted at temperatures in the range of from about 220°-250° C.

5. The method according to claim 1 wherein the pre-treatment procedure of Step (1) is conducted at a pressure of from about 200-450 psi.

6. The method according to claim 1 wherein said enzyme is selected from the group consisting of protease, cellulase, hemicellulase, pectinase, lipase, ligninase and cellulobiase.

7. The method according to claim 1 wherein said enzyme is selected from the group consisting of protease, cellulase and hemicellulase.

8. The method according to claim 1 wherein the enzymatic hydrolysis procedure of Step (4) is conducted at temperatures in the range of from about 30°-60° C. over a period of from about 1-6 hours.

9. The method according to claim 1 wherein the ground roast coffee consists essentially of extracted coffee grounds.

10. In the method for producing coffee extracts by treating an aqueous mixture of ground roast coffee with a member selected from the group consisting of a hydrolytic enzyme and a mixture of hydrolytic enzymes, the improvement which comprises: (1) pre-treating an aqueous mixture of said coffee grounds with saturated steam in a closed vessel under pressure at a temperature in excess of 200° C.; (2) maintaining said temperature and pressure for a period of from about 1-10 minutes; (3) instantaneously exposing the contents of said vessel to the atmosphere without cooling so as to bring said contents to atmospheric levels; and (4) treating the slurry thus obtained with a member selected from the group consisting of a hydrolytic enzyme and a mixture of hydrolytic enzymes.

11. The method according to claim 10 wherein the desired product is obtained as a concentrated effluent.

12. The method according to claim 11 wherein the concentrated effluent thus obtained is dried to a soluble solid.

13. The method according to claim 10 wherein the pre-treatment with saturated steam is conducted at temperatures in the range of from about 220°-250° C. and pressures of from about 200-450 psi.

14. The method according to claim 10 wherein said enzyme or mixture of enzymes is selected from the group consisting of protease, cellulase, hemicellulase, pectinase, lipase, ligninase and cellulobiase.

15. The method according to claim 10 wherein said enzyme or mixture of enzymes is selected from the group consisting of protease, cellulase and hemicellulase.

16. The method according to claim 10 wherein the enzymatic hydrolysis is conducted at temperatures in the range of from about 30°-60° C. over a period of from about 1-6 hours.

17. The method according to claim 10 wherein the ground roast coffee consists essentially of extracted coffee grounds.

* * * * *